US006322748B1

(12) United States Patent
Hutton et al.

(10) Patent No.: US 6,322,748 B1
(45) Date of Patent: Nov. 27, 2001

(54) METHOD FOR ACTIVATION OF BLEACHES

(75) Inventors: Howard David Hutton, Loveland; Kofi Ofosu-Asante, Cincinnati, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/230,435

(22) PCT Filed: Jul. 18, 1997

(86) PCT No.: PCT/US97/12216

§ 371 Date: Jan. 25, 1999

§ 102(e) Date: Jan. 25, 1999

(87) PCT Pub. No.: WO98/03622

PCT Pub. Date: Jan. 29, 1998

Related U.S. Application Data

(60) Provisional application No. 60/040,148, filed on Mar. 10, 1997, and provisional application No. 60/022,334, filed on Jul. 24, 1996.

(51) Int. Cl.[7] .......... A61L 2/12

(52) U.S. Cl. .......... 422/1; 510/375; 422/21

(58) Field of Search .......... 422/1, 21; 510/375

(56) References Cited

FOREIGN PATENT DOCUMENTS

3703049 A1 8/1988 (DE) .......... D06L/3/02
3703049-A1 * 8/1988 (DE) .......... D06L/3/02
0024304-A1 * 3/1981 (EP) .......... A61L/1/12
0 024 304 3/1981 (EP) .......... A61L/1/12
0 295 205 12/1988 (EP) .......... D06P/5/20
0295205-A1 * 12/1988 (EP) .......... D06P/5/20
2 217 204 A 10/1989 (GB) .......... A61L/2/12
WO 95/10653 4/1995 (WO) .......... D06F/18/00

OTHER PUBLICATIONS

International Preliminary Examination Report, Jun. 30, 1998, European Patent Office, International Application No. PCT/US97/12216, Applicants File Reference 6538/VB.*

* cited by examiner

*Primary Examiner*—Robert J. Warden, Sr.
*Assistant Examiner*—Sean Conley
(74) *Attorney, Agent, or Firm*—Kevin L. Waugh; Kim William Zerby; Steven W. Miller

(57) ABSTRACT

A method for removing stains or odors and for disinfecting plastics, dishware, countertops, appliances, and other substrates by activating a bleaching composition with microwaves and applying the activated composition to the substrate to be cleaned, deodorized, and/or sanitized is presented. This method provides enhanced cleaning and improved stain removal as compared to the conventional use of cleaning compositions applied directly to a substrate.

17 Claims, No Drawings

METHOD FOR ACTIVATION OF BLEACHES

This application is a 371 of PCT/US97/12216 filed Jul. 18, 1997which claims benefit of Prov. No. 60/040,148 filed Mar. 10, 1997 and Prov. No. 60/022,334 filed Jul. 24, 1996.

TECHNICAL FIELD

The present invention is in the field of bleaching compositions, preferably liquid or gel detergents. More specifically, the invention relates to a method for removing stains or odors and for disinfecting plastics, dishware, countertops, bathroom fixtures, and other substrates by activating a bleaching composition with microwaves and applying the activated composition to the substrate to be cleaned, deodorized, and/or sanitized. This method provides enhanced cleaning and improved stain removal as compared to the conventional use of cleaning compositions applied directly to a substrate.

BACKGROUND OF THE INVENTION

Detergents used for washing tableware (i.e., glassware, china, silverware, plastic, etc.), kitchenware, and household surfaces have long been known. The particular requirements of cleansing tableware and leaving it in a sanitary, essentially stainless, residue-free state has indeed resulted in so many particular compositions that the body of art pertaining thereto is now recognized as quite distinct from other cleansing product art. Likewise, the bodies of art pertaining to other household cleaning, such as fabrics, floors, hard surfaces, bathroom fixtures, are each immense and encompass many formulations designed for stain removal. Many formulations in each field include bleaches.

However, consumers continue to experience problems with stain removal on various substrates, including typical kitchenware surfaces and appliances. In particular, formulators have experienced difficulties in formulating detergents and cleaning compositions wherein the bleach is mild to the skin but has sufficient strength to perform adequately on tough stains and soils. Typically for stain removal, formulators have turned to chlorine bleach or sources of hydrogen peroxide and bleach activators.

Numerous substances have been disclosed in the art as effective bleach activators for laundry use. One widely-used bleach activator is tetraacetyl ethylene diamine (TAED). TAED provides effective hydrophilic cleaning especially on beverage stains, but has limited performance on hydrophobic stains, dingy stains and body soils. Another type of activator, such as nonanoyloxybenzenesulfonate (NOBS) and other activators which generally comprise long chain alkyl moieties, is hydrophobic in nature and provides excellent performance on dingy stains.

It would seem that a combination of bleach activators, such as TAED and NOBS, would perform well on both hydrophilic and hydrophobic soils and stains. However, many of the activators developed thus far have been found to have limited efficacy, especially at use temperatures below 60° C., which is common for dishcare and household surface cleaning. Another consideration in the development of consumer products effective on both types of soils is the additional costs associated with the inclusion of two or more bleach activators. Accordingly, it is of substantial interest to the manufacturers of bleaching systems to find a less expensive type of bleaching activator.

Chlorine bleaches are effective for stain and/or soil removal. While chlorine bleach is a very effective cleaning agent, it is not compatible with a variety of detergent ingredients and may require lengthy soaking time in which the bleach and the stained substrate must remain in contact to ensure stain removal. Another known bleaching source is diacyl peroxides (DAPs). Although DAPs have been disclosed for use in the laundry and anti-acne area, they have had limited success in liquid detergent areas. In the laundry field certain diacyl peroxides have been disclosed as beneficial in cleaning tea stains from fibrous material. It has now been discovered that DAPs can improve stain removal performance on plastics.

Another problem facing formulators is stability of the bleaching agents and other individual ingredients over time, especially in liquid products. This is particularly true for diacyl peroxides in alkaline conditions. Bleaching agents have been encapsulated to provide stability. Yet encapsulation leads to problems such as reduced dosing because of incomplete dissolution of the encapsulating material and to delayed introduction of the bleaching agent into the wash liquor.

As a consequence to the above-identified problems, there has been a substantial amount of research to develop bleaching systems which are stable and effective in liquid formulations and which remove a wide variety of stains.

By the present invention, it has now been discovered that certain bleaching agents are stable and perform very well on stains when the bleaching agent is first activated by microwaves and then applied to the substrate to be treated. Accordingly, the present invention solves the long-standing need for an inexpensive bleaching system which performs efficiently and effectively under mixed soil load conditions and is effective for a variety of substrates.

The detergent compositions provided herein have the property of removing stains, especially tea, fruit juice and carotenoid stains objected to by the consumer from plastic dishware, glass, wood, ceramic, household surfaces, and many other known substrates when the composition is first exposed to microwaves from any typical household or commercial microwave appliance. The compositions have other cleaning benefits in addition to stain removal advantages such as deodorizing and disinfecting. Thus, provided herein is a method of removing stains from a substrate by applying an activated bleaching compositions which has been subjected to microwaves.

SUMMARY OF THE INVENTION

The invention herein is a method for treating substrates comprising the steps of:

a) subjecting, in the presence of water or a solvent which generates heat under microwave radiation, a cleaning composition comprising a bleaching agent to microwaves for a sufficient period of time to activate said bleaching agent; and b) contacting a substrate with said cleaning composition.

Before microwaving, preferably water should also be present. The substrate may be wetted or dampened by water before or after application of the bleaching composition. Preferably, the bleaching composition comprises water. The compositions herein may, therefore, additionally comprise from about 0.1% to about 99.5%, more preferably from about 60–95%, even more preferably from about 80% to about 95%, by weight of the composition of water. Alternatively, a suitable solvent can be used which acts as a substitute for the water. Without being limited by theory, it is believed that the water or solvent readily generates heat when subjected to microwave radiation, which in turn, activates the bleaching agent. Suitable solvents, like water, are those with high dielectric constants. Non-limiting examples include N-alkyl pyrrolidones, such as N-ethyl pyrrolidone, diacetone alcohol, alkyl ethers, cyclic alkyl ketones, other acetyl nitriles, alcohols, and mixtures thereof. Less polar or dielectric solvents which would likely be less efficient would include non-polar hydrocarbons.

In general embodiments are provided wherein additional components, especially anionic and/or nonionic surfactant, solvent, clay, polycarboxylate thickeners, baking soda, brighteners, carbonates, phosphates, hydrobenzoic acid, dicarboxylic acid, siloxanes, perfumes, bleach catalysts, and mixtures thereof are optional; said compositions preferably have a pH of from about 3 to about 13.

Without intent to limit the types of substrates that may be treated, examples of substrates which can be treated by this method include countertops, ceramics, plastics, vinyl, metal, surgical/medical equipment, baby bottles, dishware, dentifrice/dentures, kitchen appliances, bathroom fixtures, wood, floorings, glass, and mixtures thereof. Moreover, fabrics may be treated in the wash by application of an amount of the activated cleaning composition to the wash liquor containing the fabrics to be cleaned. Examples of bleaching agents which are highly preferred for use herein included: diacyl peroxide, a source of hydrogen peroxide with or without a bleach activator, chlorine bleach and mixtures thereof.

Although this method can be employed to assist in cleaning the substrate for any desired purpose, examples of likely uses include one or more of the following: stain removal, stain reducing, deodorizing, or disinfecting. Unlike conventional cleaning or detergent compositions, the compositions of this invention are first subjected to microwaves for a sufficient time to activate the bleaching agent. It is believed that by following the method presented herein, the activated cleaning composition has enhanced performance and can significantly reduce the contact time/cleaning time necessary to treat the substrate. The substrate is contacted, typically with the addition of scrubbing or wiping, with the activated bleach composition to "treat" the substrate to the desired end result, i.e. stain reduction, deodorizing, disinfecting. Typically the bleaching composition is subjected to microwaves for a "sufficient time" in step a) to activate the bleaching agent. In general, a "sufficient time" is from about 1 second to about 2 minutes, preferably from about 2 seconds to about 30 seconds, more preferably from about 10 to about 20 seconds. This time, of course, may vary according to the type of microwave appliance and with the volume of composition to be activated.

The method herein when employed to remove or reduce stains is highly effective on hydrophobic stains such as tomato stains and dingy stains. However, the method can also be employed with very good results on hydrophilic stains such as teas stains on ceramic or other substrates.

Included below are examples of treating composition which can be employed in the method of this invention.

1 ) A sprayable liquid or sprayable gel detergent composition comprising by weight:

(a) from about 0.1% to about 60%, preferably 0.1 to about 40%, more preferably from about 0.3% to about 10%, of a bleaching agent selected from the group consisting of:

i) diacyl peroxide having the general formula:

RC(O)OO(O)CR1 wherein R and R1 can be the same or different and are hydrocarbyls, preferably no more than one is a hydrocarbyl chain of longer than ten carbon atoms, more preferably at least one has an aromatic nucleus;

ii) a source of hydrogen peroxide;

iii) a source of hydrogen peroxide and a bleach activator;

iv) a chlorine bleach, preferably hypochlorite: and v) mixtures thereof;

(b) from 0% to about 95% of a solvent;

(c) from 0% to about 50%, preferably from about 2% to about 45%, more preferably from about 8% to about 30% of an anionic or nonionic surfactant;

(d) from 0% to about 7%, preferably from about 0.5% to about 5%, more preferably from about 0.75% to about 3%, of a thickener; and (e) from about 0.1% to about 97% water.

2) A gel detergent composition especially effective at cleaning stains and tough food soil comprising by weight:

(a) from about 0.1% to about 10%, preferably 0.1 to about 8%, more preferably from about 0.3% to about 5%, of a diacyl peroxide having the general formula:

RC(O)OO(O)CR1 wherein R and R1 can be the same or different and are hydrocarbyls, preferably no more than one is a hydrocarbyl chain of longer than ten carbon atoms, more preferably at least one has an aromatic nucleus;

(b) from 0% to about 50%, preferably from about 2% to about 45%, more preferably from about 8% to about 40% of an anionic or nonionic surfactant;

(c) from 0% to about 7%, preferably from about 0.5% to about 5%, more preferably from about 0.75% to about 3%, of a thickener; and (d) from about 0. 1% to about 97% water; said composition having a neat pH of from about 3 to about 10, preferably from about 6 to about 9; and such that said diacyl peroxide remains undissolved in said compositions and acts as an abrasive.

For compositions which provide both stain removal and tough food cleaning as exemplified by 2) above, solvents are preferably not present. Without being limited by theory, it is believed that the presence of solvents may act to dissolve the diacyl peroxide and thus reduce the abrasive character of the composition. Thus, or an abrasive, tough food cleaning formulation, it is preferable that the solvent be limited to no more than about 4%, more preferably no more than about 2%, by weight of the composition.

For sprayable compositions as exemplified by 1) above, solvent may be present with any of the above identified bleaching agents. However, when diacyl peroxide is present as the bleaching agent, it is preferable to have from about 2% to about 80% of a solvent capable of dissolving the diacyl peroxide. Suitable solvents are preferably selected from the group consisting of N-alkyl pyrrolidones, such as N-ethyl pyrrolidone, diacetone alcohol, alkyl ethers, cyclic alkyl ketones, and mixtures thereof. Amines, ethers and low molecular weight primary and secondary alcohols (about $C_1$–$C_6$) are preferably not present. Without being limited by theory, it is believed that the presence of these compounds may introduce stability problems. Thus, when diacyl peroxide and solvent are present in the compositions of this invention, it is further preferable that the amount of amine, ether, or primary or secondary alcohol be limited to no more than about 5%, preferably no more than about 3%, by weight of the composition.

Specific examples of the methods encompassed by this invention are:

A method for reducing or removing stains from a stained substrate comprising the steps of:

a) subjecting, in the presence of water or a solvent which generates heat under microwave radiation, a cleaning composition comprising a bleaching agent to microwaves for a sufficient period of time to activate said bleaching agent; and b) contacting a substrate with said cleaning composition.

A method for deodorizing a substrate having an odor, said method comprises:

a) subjecting, in the presence of water or a solvent which generates heat under microwave radiation, a cleaning composition comprising a bleaching agent to microwaves for a sufficient period of time to activate said bleaching agent; and b) contacting an odorous substrate with the activated cleaning composition.

A method for disinfecting a substrate, said method comprising:

a) subjecting, in the presence of water or a solvent which generates heat under microwave radiation, a cleaning composition comprising a bleaching agent to microwaves for a sufficient period of time to activate said bleaching agent; and b) contacting a substrate containing undesirable bacteria and impurities with the activated cleaning composition.

All percentages and proportions herein are by weight, and all references cited are hereby incorporated by reference, unless otherwise specifically indicated.

DETAILED DESCRIPTION OF THE INVENTION

Definitions—The present detergent compositions comprise an "effective amount" or a "stain removal-improving amount" of a particularly defined bleaching agent. An "effective amount" or "stain removal-improving amount" of a bleaching agent is any amount capable of measurably improving stain removal (especially of tea stains and carotenoid stains) from the substrate, i.e., soiled dishware, when it is washed by the consumer. In general, this amount may vary quite widely.

By "tough food cleaning" herein is meant the ability to clean burned-on, dried-on, or baked-on foods. Examples include burned on lasagna, dried on egg, and dried on beef grease.

By "activation" herein is meant the formation of the active bleaching species from the bleaching agent. This may be by the formation of a bleaching radical or bleaching species or by the freeing of the bleaching agent from encapsulation.

Microwaves—By microwaving herein is meant exposing said cleaning composition containing a to microwave electromagnetic radiation. This is by any conventional means such as by placing the cleaning composition on a carrier, such as a sponge, cloth, or paper towel, placing the carrier in a typical microwave such as used in homes and microwaving the carrier for a sufficient time. Alternatively, the cleaning composition can be introduced into the microwave in the product container or other such container to hold an amount of the composition. Microwaves have an electromagnetic radiation wavelength of from about 1 cm to about 1 m, preferably from about 3 cm to about 30 cm, more preferably from about 11 cm to about 13 cm. See Aust. J. Chem., 1995, 48 [10], 1665–1692, Developments in Microwave-Assisted Organic Chemistry, by Strauss and Trainor.

The bleaching-containing formula may also be impregnated into the carrier and provided as a convenient product to consumers. In such a way, the consumer can merely microwave the carrier, already containing the bleaching composition and then apply the carrier to the substrate to be treated.

The compositions herein may be introduced directly into the wash liquor after activation. For example, an amount of the cleaning composition may be placed in a container and microwaved for a sufficient time to activate the bleach. The activated composition can then be introduced into a wash liquor, such as in a washing machine, soak tub, sink, or bucket, and contacted with the substrate to be treated. This is especially effective when the detergent composition used to wash the fabrics or dishes contain bleach sensitive adjuncts, such as enzymes. The activated bleaching agent may be introduced into the wash liquor at such time as to avoid negative interacts with the bleach sensitive adjuncts. In another example, the bleach agent may be encapsulated. The composition containing the encapsulated bleaching agent is subjected to microwaves to free the bleaching agent from encapsulation before use to clean the substrate. This avoids the problem of incomplete dissolution of the encapsulating material in the wash liquor or of delayed release of the bleaching agent. The bleaching agent may be encapsulated by any material and by any manner known in the art. A common encapsulating material is paraffin wax.

Bleaching Agents

Suitable bleaches for use herein are listed below:

Diacyl Peroxide Bleaching Species—The composition of the present invention preferably contain diacyl peroxide of the general formula:

RC(O)OO(O)CR1 wherein R and R1 can be the same or different and are hydrocarbyls, preferably no more than one is a hydrocarbyl chain of longer than ten carbon atoms, more preferably at least one has an aromatic nucleus.

Examples of suitable diacyl peroxides are selected from the group consisting dibenzoyl peroxide, dianisoyl peroxide, benzoyl gluaryl peroxide, benzoyl succinyl peroxide, di-(2-methybenzoyl)peroxide, diphthaloyl peroxide, dinaphthoyl peroxide, substituted dinaphthoyl peroxide, and mixtures thereof, more preferably dibenzoyl peroxide, dicumyl peroxide, diphthaloyl peroxides and mixtures thereof. A particularly preferred diacyl peroxide is dibenzoyl peroxide.

Hydrogen Peroxide Source—The compositions of the present invention may comprise a source of oxygen bleach, preferably a source of hydrogen peroxide with or without a selected bleach activator. The source of hydrogen peroxide is typically any common hydrogen-peroxide releasing salt, such as sodium perborate or sodium percarbonate. Hydrogen peroxide sources are illustrated in detail in Kirk Othmer Review on Bleaching and include the various forms of sodium perborate and sodium percarbonate and modified forms. An "effective amount" of a source of hydrogen peroxide is any amount capable of measurably improving stain removal (especially of tea and tomato stains) from the soiled substrate compared to a hydrogen peroxide source-free composition when the soiled substrate is washed by the consumer.

The preferred source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Sodium perborate monohydrate and sodium percarbonate are particularly preferred. Mixtures of any convenient hydrogen peroxide sources can also be used.

Another source of hydrogen peroxide is enzymes. Examples include Lipoxidase, glucose oxidase, peroxidase, alcohol oxidases, and mixtures thereof.

Bleach Activators—Numerous conventional bleach activators are known. See for example activators referenced herein above in the background as well as U.S. Pat. No. 4,915,854, issued Apr. 10, 1990 to Mao et al, and U.S. Pat. No. 4,412,934. Nonanoyloxybenzenesulfonate (NOBS) or acyl lactam activators may be used, and mixtures thereof with TAED can also be used. See also U.S. Pat. No. 4,634,551 for other typical conventional bleach activators. Also known are amido-derived bleach activators of the formulae: $R^1N(R^5)C(O)R^2C(O)L$ or $R^1C(O)N(R^5)R^2C(O)L$ wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is any suitable leaving group. Further illustration of bleach activators of the above formulae include (6-octanamidocaproyl)oxybenzenesulfonate, (6-nonanamidocaproyl)oxybenzenesulfonate, (6-decanamidocaproyl)oxybenzenesulfonate, and mixtures thereof as described in U.S. Pat. No. 4,634,551. Another class of bleach activators comprises the benzoxazin-type activators disclosed by Hodge et al in U.S. Pat. No. 4,966, 723, issued Oct. 30, 1990. Still another class of bleach activators includes acyl lactam activators such as octanoyl caprolactam, 3,5,5-trimethylhexanoyl caprolactam, nonanoyl caprolactam, decanoyl caprolactam, undecenoyl caprolactam, octanoyl valerolactam, decanoyl valerolactam, undecenoyl valerolactam, nonanoyl valerolactam, 3,5,5-trimethyl-hexanoyl valerolactam, t-butylbenzoylcaprolactam, t-butylbenzoylvalerolactam and mixtures thereof. The present compositions can optionally comprise aryl benzoates, such as phenyl benzoate, and acety triethyl citrate.

Quaternary Substituted Bleach Activators—The present compositions can also comprise quaternary substituted bleach activators (QSBA). QSBA's herein typically have the formula $E—[Z]_n—C(O)—L$, wherein group E is referred to as the "head", group Z is referred to as the "spacer" (n is 0 or 1, i.e., this group may be present or absent, though its presence is generally preferred) and L is referred to as the "leaving group". These compounds generally contain at least one quaternary substituted nitrogen moiety, which can be contained in E, Z or L. More preferably, a single quaternary nitrogen is present and it is located in group E or group Z. In general, L is a leaving group, the pKa of the corresponding carbon acid (HL) of which can lie in the general range from about 5 to about 30, more preferably, from about 10 to about 20, depending upon the hydrophilicity of the QSBA. pKa's of leaving groups are further defined in U.S. Pat. No. 4,283,301.

Preferred QSBA's herein are water-soluble but have a tendency to partition to a definite extent into surfactant micelles, especially into micelles of nonionic surfactants.

Leaving groups and solubilizing tendencies of quaternary moieties which can be present in the QSBA's are further illustrated in U.S. Pat. No. 4,539,130, Sep. 3, 1985 incorporated by reference. This patent also illustrates QSBA's in which the quaternary moiety is present in the leaving group L.

British Pat. 1,382,594, published Feb. 5, 1975, discloses a class of QSBA's found suitable for use herein. In these compounds, Z is a poly(methylene) or oligo(methylene) moiety, i.e., the spacer is aliphatic, and the quaternary moiety is E. U.S. Pat. No. 4.818,426 issued Apr. 4, 1989 discloses another class of QSBA's suitable for use herein. These compounds are quaternary ammonium carbonate esters wherein, with reference to the above formula, the moiety Z is attached to E via a carbon atom but is attached to the carbonyl moiety through a linking oxygen atom. These compounds are thus quaternary ammonium carbonate esters. The homologous compounds wherein the linking oxygen atom is absent from Z are likewise known and are useful herein. See, for example, U.S. Pat. No. 5,093,022 issued Mar. 3, 1992 and U.S. Pat. No. 4,904,406, issued Feb. 27, 1990. Additionally, QSBA's are described in EP 552,812 A1 published Jul. 28, 1993, and in EP 540,090 A2, published May 5, 1993.

Chlorine Bleach—Any chlorine bleach typically known in the art is suitable for use herein. Preferred chlorine bleaches for use herein include sodium hypochlorite, lithium hypochlorite, calcium hyposhlorite, chlorinated trisodium phosphates, and mixtures thereof. For more about chlorine bleaches see *Surfactant Science Series*, Vol. 5, Part II, pages 520–26.

Other Ingredients—Detersive ingredients or adjuncts optionally included in the instant compositions can include one or more materials for assisting or enhancing cleaning performance, treatment of the substrate to be cleaned, or designed to improve the aesthetics or ease of manufacture of the compositions. Other adjuncts which can also be included in compositions of the invention at their conventional art-established levels, generally from 0% to about 20% of the composition, preferably at from about 0.1% to about 10%, include one or more processing aids, color speckles, dyes, fillers, enzymes, germicides, alkalinity sources, hydrotropes, stabilizers, perfumes, solubilizing agents, carriers. In general, materials used for the production of detergent compositions herein are preferably checked for compatibility with the essential ingredients used herein.

In the preferred embodiments, additional ingredients such as water-soluble silicates (useful to provide alkalinity and assist in controlling corrosion), dispersant polymers (which modify and inhibit crystal growth of calcium and/or magnesium salts), chelants (which control transition metals), builders such as citrate (which help control calcium and/or magnesium and may assist buffering action), alkalis (to adjust pH), and detersive enzymes (to assist with tough food cleaning, especially of starchy and proteinaceous soils) are present. Additional bleach-improving materials such as bleach catalysts may be added.

Solvent—The solvent of the present invention is of the type which the diacyl peroxide will dissolve in. The preferred solvents are selected based upon the solubility parameter value of the diacyl peroxide employed. The solubility parameter value of a compound is available from literature sources such as Polymer Handbook. Values obtained by experiments are preferred. If the solubility parameter value is not available in the literature, the value can be calculated by using any of the methods described by Robert F. Fedor's article "A Method of Estimating Both the Solubility Parameters & Molar Volumes of Liquids", Polymer Engineering & Science, February, 1974, Vol 14, No. 2. Once the solubility parameter value is obtained of the diacyl peroxide, solvents are selected having a solubility parameter which fall within the diacyl peroxide solubility parameter.

Said solvent is preferably selected from the group consisting of N-alkyl pyrrolidones, such as N-ethyl pyrrolidone, diacetone alcohol, long chain (greater than $C_6$) alkyl ethers, cyclic alkyl ketones, and mixtures thereof. Amines, ethers and short chain (less than $C_6$) primary and secondary alcohols are preferably not present. Without being limited by theory, it is believed that the presence of these compounds may introduce stability problems. Thus, when diacyl peroxide and solvent are present in the compositions of this invention, it is further preferable that the amount of amine, ether, or primary or secondary alcohol be limited to no more than about 5%, preferably no more than about 3%, by weight of the composition.

Process Description—The diacyl peroxide raw material particles are dissolved in an appropriate solvent (n-ethylpyrrolidone) and added to the rest of the fomulation (primarily water, surfactant and thickener) with stirring. This procedure results in the in situ precipitation of the diacyl peroxide particles, resulting in a dispersion of small homogeneous particles ranging in sized of from about 1 to about 20 microns. In another processing method, the diacyl peroxide particles may be formed by any known method of shear mixing. The diacyl particles for use herein can range in size from sub-micron (0.1 ) to about 100 microns. A preferred range is from about 1 to about 20 microns.

Surfactants—Nonlimiting examples of surfactants useful herein include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3$—$M^+)$ $CH_3$ and $CH_3$ $(CH_2)_y(CHOSO_{03}$—$M^+)CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("$AE_xS$"; especially EO 1–7 ethoxy sulfates), $C_{10}$–$C_{18}$ alkyl alkoxy carboxylates (especially the EO 1–5 ethoxycarboxylates), the $C_{10}$–$C_{18}$ glycerol ethers, the $C_{10}$–$C_{18}$ alkyl polyglycosides and their corresponding sulfated polyglycosides, and $C_{12}$–$C_{18}$ alpha-sulfonated fatty acid esters.

If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), $C_{12}$–$C_{18}$ betaines and sulfobetaines ("sultaines"), and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Other conventional useful surfactants are listed in standard texts.

Preferably, anionic surfactants are used herein. Without being limited by theory, it is believed that the use of anionic surfactants maximizes both cleaning performance and removal of residual bleach from the substrate being treated.

One example of a group of surfactants suitable for use herein are those selected from the group consisting of alkyl ether sulfate, long chain ($C_7$ or greater) alky ethoxylate, linear alkyl benzene sulfonate (LAS), alkyl (ether) carboxylates, alkyl polyglucaside (APG), and mixtures thereof. Cationic surfactants are not preferred for use herein.

Thickeners—Thickeners for use herein include those selected from clay, polycarboxylates, such as Polygel®, gums, carboxymethyl cellulose, polyacrylates, and mixtures thereof. The preferred clay type herein has a double-layer structure. The clay may be naturally occurring, e.g., Bentonites, or artificially made, e.g., Laponite®. Laponite® is supplied by Southern Clay Products, Inc. See *The Chemistry and Physics of Clays*, Grimshaw, 4th ed., 1971, pages 138–155, Wiley-Interscience.

Bleach catalysts—If desired, detergent compositions herein may additionally incorporate a catalyst or accelerator to further improve bleaching or starchy soil removal. Any suitable bleach catalyst can be used. The compositions will comprise from about 0.0001% to about 0. 1% by weight of bleach catalyst.

Typical bleach catalysts comprise a transition-metal complex, for example one wherein the metal co-ordinating ligands are quite resistant to labilization and which does not deposit metal oxides or hydroxides to any appreciable extent under the conditions of cleaning herein. Such catalyst compounds often have features of naturally occurring compounds such as enzymes but are principally provided synthetically. Highly preferred accelerators include, for example, the cobalt 3+ catalysts, especially $\{Co(NH_3)_5Cl\}^{2+}$ or equivalents thereof with various alternate donor ligands. Such complexes include those formerly disclosed for use in laundry compositions in U.S. Pat. No. 4,810,410 to Diakun et al, issued Mar. 7, 1989. The active species thereof is believed to be $\{Co(NH_3)_5(OOH)\}^{2+}$ and is disclosed in J. Chem. Soc. Faraday Trans., 1994, Vol. 90, 1105–1114. Alternate catalysts or accelerators are the non-cobalt transition metal complexes disclosed in this reference, especially those based on Mo(VI), Ti(IV), W(VI), V(V) and Cr(VI) although alternate oxidation states and metals may also be used. Such catalysts include manganese-based catalysts disclosed in U.S. Pat. Nos. 5,246,621, 5,244,594; 5,194,416; 5,114,606; and EP Nos. 549,271 A1, 549,272 A1, 544,440 A2, and 544,490 A1; preferred examples of these catalysts include $Mn^{IV}_2(\mu\text{-}O)_3(TACN)_2\text{-}(PF_6)_2$, $Mn^{III}_2(\mu\text{-}O)_1(\mu\text{-}OAc)_2(TACN)_2(ClO_4)_2$, $Mn^{IV}_4(\mu\text{-}O)_6(TACN)_4(ClO_4)_4$, $Mn^{III}Mn^{IV}_4\text{-}(\mu\text{-}O)_1(\mu\text{-}OAc)_2\text{-}(TACN)_2\text{-}(ClO_4)_3$, $Mn^{IV}\text{-}(TACN)\text{-}(OCH_3)_3(PF_6)$, and mixtures thereof wherein TACN is trimethyl- 1,4,7-triazacyclononane or an equivalent macrocycle; though alternate metal-co-ordinating ligands as well as mononuclear complexes are also possible and monometallic as well as di- and polymetallic complexes and complexes of alternate metals such as iron or ruthenium are all within the present scope. Other metal-based bleach catalysts include those disclosed in U.S. Pat. Nos. 4,430,243 and 5,114,611. The use of manganese with various complex ligands to enhance bleaching is also reported in the following U.S. Pat. Nos. 4,728,455; 5,284.944; 5.246,612; 5,256,779; 5,280,117; 5,274,147; 5,153,161; and 5,227,084.

Transition metals may be precomplexed or complexed in-situ with suitable donor ligands selected in function of the choice of metal, its oxidation state and the denticity of the ligands. Other complexes which may be included herein are those of U.S. application Ser. No. 08/210,186, filed Mar. 17, 1994. Other suitable transition metals in said transition-metal-containing bleach catalysts include iron, cobalt, ruthenium, rhodium, iridium, and copper.

Builders—Detergent builders can optionally be included in the compositions herein to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least about 1% builder. Liquid formulations typically comprise from about 5% to about 50%, more typically about 5% to about 30%, by weight, of detergent builder. Lower or higher levels of builder, however, are not meant to be excluded.

Inorganic or P-containing detergent builders include, but are not limited to, the alkali metal, ammonium and alkanolammonium salts of polyphosphates (exemplified by the tripolyphosphates, pyrophosphates, and glassy polymeric metaphosphates), phosphonates, phytic acid, silicates, carbonates (including bicarbonates and sesquicarbonates), sulphates, and aluminosilicates.

Examples of silicate builders are the alkali metal silicates, particularly those having a $SiO_2$:$Na_2O$ ratio in the range 1.6:1 to 3.2:1 and layered silicates, such as the layered sodium silicates described in U.S. Pat. No. 4,664,839, issued May 12, 1987 to H. P. Rieck. NaSKS-6 is the trademark for a crystalline layered silicate marketed by Hoechst (commonly abbreviated herein as "SKS-6"). NaSKS-6 can be prepared by methods such as those described in German DE-A-3,417,649 and DE-A-3,742,043. Other layered silicates, such as those having the general formula $NaMSi_xO_{2x+1}.yH_2O$ wherein M is sodium or hydrogen, x is a number from 1.9 to 4, preferably 2, and y is a number from 0 to 20 can be used herein. Various other layered silicates from Hoechst include NaSKS-5, NaSKS-7 and NaSKS-11, as the alpha, beta and gamma forms. Examples of carbonate builders are the alkaline earth and alkali metal carbonates as disclosed in German Patent Application No. 2,321,001 published on Nov. 15,1973.

Aluminosilicate builders may be useful in the present invention. Aluminosilicate builders include those having the empirical formula:

$$M_z(zAlO_2)_y]\cdot xH_2O$$

wherein z and y are integers of at least 6, the molar ratio of z to y is in the range from 1.0 to about 0.5, and x is an integer from about 15 to about 264.

Useful aluminosilicate ion exchange materials are commercially available. A method for producing aluminosilicate ion exchange materials is disclosed in U.S. Pat. No. 3,985, 669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula:

$$Na_{12}[(AlO_2)_{12}(SiO_2)_{12}]\cdot xH_2O$$

wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of importance for liquid detergent formulations due to their availability from renewable resources and their biodegradability. Oxydisuccinates are also especially useful in such compositions and combinations.

Also suitable in the compositions of the present invention are the 3,3-dicarboxy-4-oxa- 1,6-hexanedioates and the related compounds disclosed in U.S. Pat. No. 4,566,984, Bush, issued Jan. 28, 1986. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also Diehl U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity.

Various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Enzymes—Suitable enzymes include proteases, amylases, lipases, cellulases, peroxidases, and mixtures thereof of any suitable origin, such as vegetable, animal. bacterial, fungal and yeast origin. Preferred selections are influenced by factors such as pH-activity and/or stability optima, thermostability, and stability to active bleach, detergents, builders and the like. In this respect bacterial or fungal enzymes are preferred, such as bacterial amylases and proteases, and fungal cellulases.

Enzymes are normally incorporated into detergent or detergent additive compositions at levels sufficient to provide a "cleaning-effective amount". The term "cleaning effective amount" refers to any amount capable of producing a cleaning, stain removal, soil removal, whitening, deodorizing, or freshness improving effect on substrates such as dishware and the like. In practical terms for current commercial preparations, the compositions herein may comprise from 0.001% to 5%, preferably 0.01%–1% by weight of a commercial enzyme preparation. Protease enzymes are usually present in such commercial preparations at levels sufficient to provide from 0.005 to 0.1 Anson units (AU) of activity per gram of composition.

The preparation of protease enzyme and analogous enzymes is described in GB 1,243,784 to Novo. Other suitable proteases include ALCALASE® and SAVINASE® from Novo and MAXATASE® from International Bio-Synthetics, Inc., The Netherlands; as well as Protease A as disclosed in EP 130,756 A, Jan. 9, 1985 and Protease B as disclosed in EP 303,761 A, Apr. 28, 1987 and EP 130,756 A, Jan. 9, 1985. See also a high pH protease from Bacillus sp. NCIMB 40338 described in WO 9318140 A to Novo. Enzymatic detergents comprising protease, one or more other enzymes, and a reversible protease inhibitor are described in WO 9203529 A to Novo. Other preferred proteases include those of WO 9510591 A to Procter & Gamble. When desired, a protease having decreased adsorption and increased hydrolysis is available as described in WO 9507791 to Procter & Gamble. A recombinant trypsin-like protease for detergents suitable herein is described in WO 9425583 to Novo.

Amylases suitable herein, especially for, but not limited to automatic dishwashing purposes, include, for example, α-amylases described in GB 1,296,839 to Novo; RAPIDASE®, International Bio-Synthetics, Inc. and TERMAMYL®, Novo. FUNGAMYL® from Novo is especially useful. Engineering of enzymes for improved stability, e.g., oxidative stability, is known. See, for example J. Biological Chem., Vol. 260, No. 11, June 1985, pp 6518–6521 Preferred amylases include (a) an amylase according to the hereinbefore incorporated WO 9402597, Novo, Feb. 3, 1994. Other amylases include variants having additional modification in the immediate parent as described in WO 9510603 A and are available from the assignee, Novo, as DURAMYL®. Other particularly preferred oxidative stability enhanced amylase include those described in WO 9418314 to Genencor International and WO 9402597 to Novo.

Cellulases usable herein include those disclosed in U.S. Pat. No. 4,435,307, Barbesgoard et al, Mar. 6, 1984. Suitable cellulases are also disclosed in GB-A-2.075.028; GB-A-2.095.275 and DE-OS-2.247.832. CAREZYME® (Novo) is especially useful. See also WO 9117243 to Novo.

Suitable lipase enzymes for detergent usage include those produced by microorganisms of the Pseudomonas group, such as *Pseudomonas stutzeri* ATCC 19.154, as disclosed in GB 1,372,034. See also lipases in Japanese Patent Application 53,20487, laid open Feb. 24, 1978. Other suitable commercial lipases include Amano-CES, lipases ex *Chromobacter viscosum,* e.g. *Chromobacter viscosum* var. lipolyticum NRRLB 3673 from Toyo Jozo Co., Tagata, Japan; *Chromobacter viscosum* lipases from U.S. Biochemical Corp., U.S.A. and Disoynth Co., The Netherlands, and lipases ex *Pseudomonas gladioli*. LIPOLASE® enzyme derived from *Humicola lanuginosa* and commercially available from Novo, see also EP 341,947, is a preferred lipase for use herein. Lipase and amylase variants stabilized against peroxidase enzymes are described in WO 9414951 A to Novo. See also WO 9205249 and RD 94359044.

Cutinase enzymes suitable for use herein are described in WO 8809367 A to Genencor.

Peroxidase enzymes may be used in combination with oxygen sources, e.g., percarbonate, perborate, hydrogen peroxide, etc., for "solution bleaching" or prevention of transfer of dyes or pigments removed from substrates during the wash to other substrates present in the wash solution. Known peroxidases include horseradish peroxidase, ligninase, and haloperoxidases such as chloro- or bromo-peroxidase. Peroxidase-containing detergent compositions are disclosed in WO 89099813 A, Oct. 19, 1989 to Novo and WO 8909813 A to Novo.

A range of enzyme materials and means for their incorporation into synthetic detergent compositions is also disclosed in WO 9307263 A and WO 9307260 A to Genencor International, WO 8908694 A to Novo, and U.S. Pat. No. 3,553,139, Jan. 5, 1971 to McCarty et al. Enzymes are further disclosed in U.S. Pat. No. 4,101,457, Place et al, Jul. 18, 1978, and in U.S. Pat. No. 4,507,219, Hughes, Mar. 26, 1985. Enzyme materials useful for liquid detergent formulations, and their incorporation into such formulations, are disclosed in U.S. Pat. No. 4,261,868, Hora et al, Apr. 14, 1981. Enzymes for use in detergents can be stabilised by various techniques. Enzyme stabilisation techniques are disclosed and exemplified in U.S. Pat. No. 3,600,319, Aug. 17, 1971, Gedge et al, EP 199,405 and EP 200,586, Oct. 29, 1986, Venegas. Enzyme stabilisation systems are also described, for example, in U.S. Pat. No. 3,519,570. A useful Bacillus, sp. AC 13 giving proteases, xylanases and cellulases, is described in WO 9401532 A to Novo.

Enzyme Stabilizing System—Enzyme-containing, including but not limited to, liquid compositions, herein may comprise from about 0.001% to about 10%, preferably from about 0.005% to about 8%, most preferably from about 0.01% to about 6%, by weight of an enzyme stabilizing system. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition. See Severson, U.S. Pat. No. 4,537,706 for a review of Borate stabilizers.

Stabilizing systems may further comprise from 0 to about 10%, preferably from about 0.01% to about 6% by weight, of chlorine bleach scavengers, added to prevent chlorine bleach species present in many water supplies from attacking and inactivating the enzymes, especially under alkaline conditions. Suitable chlorine scavenger anions are widely known and readily available, and, if used, can be salts containing ammonium cations with sulfite, bisulfite. thiosulfite, thiosulfate, iodide, etc. Antioxidants such as carbamate, ascorbate, etc., organic amines such as ethylenediaminetetracetic acid (EDTA) or alkali metal salt thereof, monoethanolamine (MEA), and mixtures thereof can likewise be used. Other conventional scavengers such as bisulfate, nitrate, chloride, sources of hydrogen peroxide such as sodium perborate tetrahydrate, sodium perborate monohydrate and sodium percarbonate, as well as phosphate, condensed phosphate, acetate, benzoate, citrate, formate, lactate, malate, tartrate, salicylate, etc., and mixtures thereof can be used if desired.

Material Care Agents—The present compositions may optionally contain as corrosion inhibitors and/or anti-tarnish aids one or more material care agents such as silicates. Material Care Agents are preferred especially in countries where electroplated nickel silver and sterling silver are common in domestic flatware, or when aluminium protection is a concern and the composition is low in silicate. Material care agents include bismuth salts, transition metal salts such as those of manganese, certain types of paraffin, triazoles, pyrazoles, thiols, mercaptans, aluminium fatty acid salts, and mixtures thereof and are preferably incorporated at low levels, e.g., from about 0.01% to about 5% of the composition. A preferred paraffin oil is a predominantly branched aliphatic hydrocarbon comprising from about 20 to about 50, more preferably from about 25 to about 45, carbon atoms with a ratio of cyclic to noncyclic hydrocarbons of about 32 to 68 sold by Wintershall, Salzbergen, Germany as WINOG 70®. $Bi(NO_3)_3$ may be added. Other corrosion inhibitors are illustrated by benzotriazole, thiols including thionaphtol and thioanthranol, and finely divided aluminium fatty acid salts. All such materials will generally be used judiciously so as to avoid producing spots or films on glassware or compromising the bleaching action of the compositions. For this reason, it may be preferred to formulate without mercaptan anti-tarnishes which are quite strongly bleach-reactive or common fatty carboxylic acids which precipitate with calcium.

Chelating Agents—The detergent compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined.

Amino carboxylates useful as optional chelating agents include ethylenediaminetetracetates, N-hydroxyethylethylenediaminetriacetates, nitrilotriacetates, ethylenediamine tetraproprionates, triethylenetetra-amine-hexacetates, diethylenetriaminepentaacetates, and ethanoldiglycines, alkali metal, ammonium, and substituted ammonium salts therein and mixtures therein.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene. A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

If utilized, these chelating agents will generally comprise from about 0.1% to about 10% by weight of the detergent compositions herein. More preferably, if utilized, the chelating agents will comprise from about 0.1% to about 3.0% by weight of such compositions.

Polymeric Dispersing Agents—Polymeric dispersing agents can advantageously be utilized at levels from about 0.1% to about 7%, by weight, in the compositions herein, especially in the presence of zeolite and/or layered silicate builders. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition.

Brightener—Any optical brighteners or other brightening or whitening agents known in the art can be incorporated at levels typically from about 0.05% to about 1.2%, by weight, into the detergent compositions herein. Commercial optical brighteners which may be useful in the present invention can be classified into subgroups, which include, but are not necessarily limited to, derivatives of stilbene, pyrazoline, coumarin, carboxylic acid, methinecyanines, dibenzothiphene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982).

Polymeric Soil Release Agent—Any polymeric soil release agent known to those skilled in the art can optionally be employed in the compositions and processes of this invention. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of washing and rinsing cycles and, thus, serve as an anchor for the hydrophilic segments. This can enable stains occurring subsequent to treatment with the soil release agent to be more easily cleaned in later washing procedures. If utilized, soil release agents will generally comprise from about 0.01% to about 10.0%, by weight, of the detergent compositions herein, typically from about 0.1% to about 5%, preferably from about 0.2% to about 3.0%.

Polymeric Dispersing Agents—Polymeric dispersing agents can advantageously be utilized at levels from about 0.1% to about 7%, by weight, in the compositions herein, especially in the presence of zeolite and/or layered silicate builders. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition.

Microwaves—By microwaving herein is meant exposing said substrate treated with said compositions to microwave electromagnetic radiation. This is by any conventional means such as by placing the substrate in a typical microwave such as used in homes and microwaving the substrate for a sufficient time. Microwaves have an electromagnetic radiation wavelength of from about 1 cm to about 1 m, preferably from about 3 cm to about 30 cm, more preferably from about 11 cm to about 13 cm. See Aust. J. Chem., 1995, 48[10], 1665–1692, Developments in Microwave-Assisted Organic Chemistry, by Strauss and Trainor.

Process Description—The diacyl peroxide raw material particles are dissolved in an appropriate solvent (n-ethylpyrrolidone) and added to the rest of the fomulation (primarily water, surfactant and thickener) with stirring. This procedure results in the in situ precipitation of the diacyl peroxide particles, resulting in a dispersion of small homogeneous particles ranging in size of from about 1 to about 20 microns. In another processing method, the diacyl peroxide particles may be formed by any known method, including shear mixing. The diacyl particles for use herein can range in size from sub-micron (0.1) to about 100 microns. A preferred range is from about 1 to about 20 microns.

Procedure for preparation of in situ particles: Laponite (33 g, 6% active) is dispersed in tap water (100 g) with stirring. Sodium Alkylethoxy sulfate (14 g, 70% active) is stirred into the Laponite dispersion and Sodium bicarbonate (1 g, 100% active) is added. In a separate container, Benzoyl peroxide (2 g, 75% active) is dissolved in N-ethylpyrrolidone (10 g, 100% active) with stirring. This benzoyl peroxide solution is then poured into the Laponite and surfactant solution with stirring. The mixture immediately turns cloudy and results in a homogeneous dispersion of 10–50 micron benzoyl peroxide particles.

Product/Instructions—This invention also encompasses the inclusion of instructions on the use of the cleaning composition with the package containing the cleaning compositions herein or with other forms of advertising associated with the sale or use of the cleaning compositions. The instructions may be included in any manner typically used by consumer product manufacturing or supply companies. Examples include providing instructions on a label attached to the container holding the composition; on a sheet either attached to the container or accompanying it when purchased; or in advertisements, demonstrations, and/or other written or oral instructions which may by connected to the purchase or use of the cleaning compositions.

Specifically the instructions will include a description of the use of the cleaning composition in connection with microwaving. The instructions, for instance, may additionally include information relating to the length of microwaving time; the recommended settings on the microwave; the recommended amount of treating composition to apply to the substrate, if soaking or rubbing is appropriate to the substrate; the recommended amount of water, if any, to apply to the substrate before and after treatment; other recommended treatment to accompany the microwave application.

A product comprising a cleaning composition comprising a bleaching agent and instructions for use of the cleaning composition, said instructions include the steps of:

a) subjecting, in the presence of water or a solvent which generates heat under microwave radiation, (either in the product or supplied separately), said cleaning composition to microwaves for a sufficient period of time to activate said bleaching agent; and b) contacting a substrate with said cleaning composition.

EXAMPLE I

| Ingredient | A nil Acyl Deroxide | B Non-activated Acyl peroxide | C Activated Acyl Deroxide |
|---|---|---|---|
| $C_{12-13}$ alkyl ether sulfate (avg. ethoxy of 1) | 12 | 12 | 12 |
| Potassium bicarbonate | 0.8 | 0.8 | 0.8 |
| Alkyl pyrrolidinone | 5 | 5 | 5 |
| Acyl peroxide[1] | — | 1 | 1 |
| Perfume | 0.2 | 0.2 | 0.2 |
| Other (water, dye etc.) | to 100% | to 100% | to 100% |
| | Stain Removal Performance | | |
| Tomato | poor | good | excellent |
| Tea | poor | good | excellent |

[1]Acyl Peroxides selected from benzoyl peroxide, dilauroyl, dianisoyl.

A Formica countertop is stained by heated tomato sauce and tea under typical consumer conditions by contacting the countertop with the heated sauce and tea for 6 hours. The stained countertop is washed with a conventional light duty liquid dishwashing detergent, commercially available, under typical home wash conditions. The countertop remains stained by the tomato and tea. An amount of each of the above compositions is applied to a sponge. In Example C the treated sponge is placed in a typical household microwave and microwaved on high setting for 15–30 seconds. The sponge for each Example is then used to wipe the surface of a Formica countertop which has been stained with tomato sauce. The countertop is then rinsed with water. The percent removal is estimated visually based on comparison with a stained control and a clean control. As can be seen in the example, in A without bleaching agent has poor stain removal ability. Examples B has good stain removal ability but with activation Example C shows excellent stain removal ability.

EXAMPLE II

| Ingredient | A Acyl peroxide with Polygel | B Acyl peroxide with Laponite |
|---|---|---|
| $C_{10}$ alkyl ethoxylate (avg. ethoxy of 10) | 5 | 5 |
| $C_{12-13}$ alkyl ether sulfate (avg. ethoxy of 1) | 14.5 | 14.5 |
| Magnesium chloride hexahydrate | 0.3 | 0.3 |
| Magnesium silicate[1] | 2 | 2 |
| Potassium bicarbonate | 1 | 1 |
| Alkyl pyrrolidinone | 15 | 15 |
| Acyl peroxide[3] | 2 | 2 |
| Perfume | 0.18 | 0.18 |
| Other (water, dye etc.) | to 100% | to 100% |
| | Stain Removal Performance | |
| Tomato | fair | very good |
| Tea | fair | very good |

[1]Commercially available as Laponite RD ®
[2]Commercially available as Polygel DK ®
[3]Acyl Peroxide selected from benzoyl peroxide, dilauroyl, dianisol.

Dishes and plastic bowls are stained by heated tomato sauce and tea under typical consumer conditions by contacting the items with the heated sauce and tea for 6 hours. The stained items are washed with a conventional automatic dishwashing detergent, commercially available, under typical home wash conditions in an automatic dishwashing machine. The items remain stained by the tomato and tea. One-fourth cup of B is placed in a typical household microwave and microwaved on high setting for 20–30 seconds. One-fourth cup of A is not microwaved. The compositions are then poured into or wiped onto the stained dishes and allowed to sit for 20 minutes. The items are next washed with the aid of a typical household dish detergent and rinsed with water. The percent removal is estimated visually based on comparison with a stained control and a clean control. Both formulas show some degree of performance, although Example B which has been microwaved is superior.

EXAMPLE III

| Stain/Surface | Microwave Application A | Direct Application B | Commercial Product C |
|---|---|---|---|
| Juice on formica (% removal) | 73 | 36 | 31 |
| Tea on formica (% removal) | 22 | 28 | 18 |

Formula A of Example II is compared after microwaving to the same composition without microwaving and against a commercially available non-bleach countertop cleaner, sold under the name FORMULA 409™ and made by Clorox Co.

The formulas are applied to a standard household sponge which has been dampened by water. In column A, the formula is exposed to microwaves in a household microwave for 30 seconds. In Columns B and C, no microwaves are applied to the formula. The sponge is then contacted with formica which has been stained with juice or tea. As can be seen, the microwaved bleach-containing formula provides significantly better stain removal of juice on formica and comparable performance on tea stains.

What is claimed is:

1. A method for treating a plastic or ceramic kitchenware, dishware or household substrate comprising the steps of:

a) subjecting, in the presence of water or a solvent which generates heat under microwave radiation, a cleaning composition comprising a diacyl peroxide bleaching agent to microwaves for a sufficient period of time to activate said bleaching agent; and b) contacting said substrate with said cleaning composition.

2. A method according to claim 1 wherein said diacyl peroxide is selected from the group consisting of dibenzoyl peroxide, dianisoyl peroxide, benzoyl gluaryl peroxide, benzoyl succinyl peroxide, di-(2-methylbenzoyl)peroxide, diphthaloyl peroxide, dinaphthoyl peroxide, substituted dinaphthoyl peroxide, and mixtures thereof.

3. A method according to claim 1 wherein said substrate is treated for one or more of the following: stain removal, stain reducing, deodorizing, or disinfecting.

4. A method according to claim 1 wherein said cleaning composition further comprises at least one additional component selected from the group consisting of anionic surfactant, nonionic surfactant, solvent, clay, water, polycarboxylate thickeners, baking soda, carbonates, phosphates, hydrobenzoic acid, dicarboxylic acid, siloxanes, perfumes, and bleach catalysts, and mixtures thereof.

5. A method according to claim 4 wherein said cleaning composition is a sprayable liquid.

6. A method according to claim 4 wherein said cleaning composition is a gel.

7. A method according to claim 1 wherein said sufficient time in step a) is from about 1 second to about 2 minutes.

8. A method according to claim 1 wherein the activated composition is introduced into a wash liquor containing the substrate to be treated.

9. A method according to claim 1 wherein said cleaning composition is a sprayable liquid or sprayable gel composition, comprising by weight:

(a) from about 0.1% to about 60% of a diacyl peroxide having the general formula:

RC(O)OO(O)CR1 wherein R and R1 can be the same or different;

(b) from 0% to about 95% of a solvent;

(c) from 0% to about 50% of an anionic or nonionic surfactant;

(d) from 0% to about 7% of a thickener; and (e) from about 0.1% to about 97% water.

10. A method according to claim 9 wherein said cleaning composition is a gel detergent composition and wherein said diacyl peroxide is selected from the group consisting of dibenzoyl peroxide, dianisoyl peroxide, benzoyl gluaryl peroxide, benzoyl succinyl peroxide, di-(2-methylbenzoyl) peroxide, diphthaloyl peroxide, dinaphthoyl peroxide, substituted dinaphthoyl peroxide, and mixtures thereof.

11. A method according to claim 1 wherein said cleaning composition is especially effective at cleaning stains and tough food soil, said cleaning composition comprises by weight:

(a) from about 0.1% to about 10% of a diacyl peroxide having the general formula:

RC(O)OO(O)CR1 wherein R and R1 can be the same or different and are hydrocarbyls;

(b) from 0% to about 50% of an anionic or nonionic surfactant;

(c) from 0% to about 7% of a thickener; and (d) from about 0.1% to about 97% water;

said composition having a neat pH of from about 3 to about 10; and wherein said diacyl peroxide remains undissolved in said composition.

12. A method according to claim 1 wherein the cleaning composition is applied to a carrier before subjected to microwaves in step a).

13. A method according to claim 12 wherein said carrier is impregnated with said cleaning composition.

14. A method according to claim 12 wherein said carrier is selected from the following: sponge, paper towel, cloth, or towel.

15. A method according to claim 1 wherein the substrate is plastic.

16. A product comprising a cleaning composition comprising a diacyl peroxide bleaching agent and instructions for use of the cleaning composition, said instructions include the steps of:

a) subjecting, in the presence of water or a solvent which generates heat under microwave radiation, said cleaning composition to microwaves for a sufficient period of time to activate said bleaching agent; and b) contacting a plastic or ceramic kitchenware, dishware or household substrate with said cleaning composition.

17. A product according to claim 9 wherein the substrate is plastic.

* * * * *